United States Patent
Hayashi (10) Patent No.: US 11,493,471 B2
(45) Date of Patent: Nov. 8, 2022

(54) SENSOR

(71) Applicant: KABUSHIKI KAISHA TOSHIBA, Tokyo (JP)

(72) Inventor: Yumi Hayashi, Ayase Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 17/407,050

(22) Filed: Aug. 19, 2021

(65) Prior Publication Data

US 2022/0268723 A1     Aug. 25, 2022

(30) Foreign Application Priority Data

Feb. 22, 2021   (JP) .............................. JP2021-025908

(51) Int. Cl.
  *G01N 27/22* (2006.01)
  *G01N 33/00* (2006.01)

(52) U.S. Cl.
  CPC ......... *G01N 27/226* (2013.01); *G01N 27/221* (2013.01); *G01N 33/0027* (2013.01)

(58) Field of Classification Search
  CPC . G01N 27/226; G01N 27/221; G01N 33/0027
  See application file for complete search history.

(56) References Cited

U.S. PATENT DOCUMENTS

| | | | |
|---|---|---|---|
| 2010/0295138 A1* | 11/2010 | Montanya Silvestre | H01L 24/05 257/415 |
| 2016/0167954 A1* | 6/2016 | Gogoi | H01L 27/14 257/415 |
| 2016/0282259 A1* | 9/2016 | Kolb | G01N 29/022 |
| 2017/0030857 A1* | 2/2017 | Pantel | G01N 27/4073 |
| 2019/0086377 A1 | 3/2019 | Ikehashi et al. | |
| 2019/0162694 A1 | 5/2019 | Hayashi | |
| 2019/0301908 A1* | 10/2019 | Kisban | G01F 1/6845 |

FOREIGN PATENT DOCUMENTS

| JP | 2019-56607 A | 4/2019 |
|---|---|---|
| JP | 2019-100705 A | 6/2019 |

OTHER PUBLICATIONS

T. Tanaka et al., "Nanoscale Pt thin film sensor for accurate detection of ppm level hydrogen in air at high humidity," Sensors and Actuators B: Chemical, vol. 258, pp. 913-919 (2018).

* cited by examiner

*Primary Examiner* — Alvaro E Fortich
(74) *Attorney, Agent, or Firm* — Finnegan, Henderson, Farabow, Garrett & Dunner L.L.P.

(57) ABSTRACT

According to one embodiment, a sensor includes a first sensor part. The first sensor part includes a first counter electrode, a first movable electrode, a first layer, and a first intermediate layer. The first movable electrode is between the first counter electrode and the first layer. The first intermediate layer is between the first movable electrode and a portion of the first layer. A first gap is located between the first counter electrode and the first movable electrode. A distance between the first counter electrode and the first movable electrode changes according to a concentration of a gas around the first sensor part. The first layer includes a crystal. The first intermediate layer is amorphous, or a crystallinity of the first intermediate layer is less than a crystallinity of the first layer. A width of the first layer is greater than a width of the first intermediate layer.

20 Claims, 8 Drawing Sheets

)
SENSOR

CROSS-REFERENCE TO RELATED APPLICATIONS

This application is based upon and claims the benefit of priority from Japanese Patent Application No. 2021-025908, filed on Feb. 22, 2021; the entire contents of which are incorporated herein by reference.

FIELD

Embodiments described herein relate generally to a sensor.

BACKGROUND

For example, stable detection is desirable in a sensor.

DETAILED DESCRIPTION

According to one embodiment, a sensor includes a first sensor part. The first sensor part includes a first counter electrode, a first movable electrode, a first layer, and a first intermediate layer. The first movable electrode is between the first counter electrode and the first layer in a first direction. The first intermediate layer is between the first movable electrode and at least a portion of the first layer in the first direction. A first gap is located between the first counter electrode and the first movable electrode. A distance between the first counter electrode and the first movable electrode changes according to a concentration of a gas around the first sensor part. The first layer includes a crystal. The first intermediate layer is amorphous, or a crystallinity of the first intermediate layer is less than a crystallinity of the first layer. A width of the first layer along a second direction is greater than a width of the first intermediate layer along the second direction. The second direction crosses the first direction.

According to one embodiment, a sensor includes a second sensor part. The second sensor part includes an insulating member and a resistance member. The resistance member includes a second layer, and a second intermediate layer located between the insulating member and at least a portion of the second layer in a first direction. An electrical resistance of the resistance member changes according to a concentration of a gas around the second sensor part. The second layer includes a crystal. The second intermediate layer is amorphous, or a crystallinity of the second intermediate layer is less than a crystallinity of the second layer. A width of the second layer along a second direction is greater than a width of the second intermediate layer along the second direction. The second direction crosses the first direction.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1A:
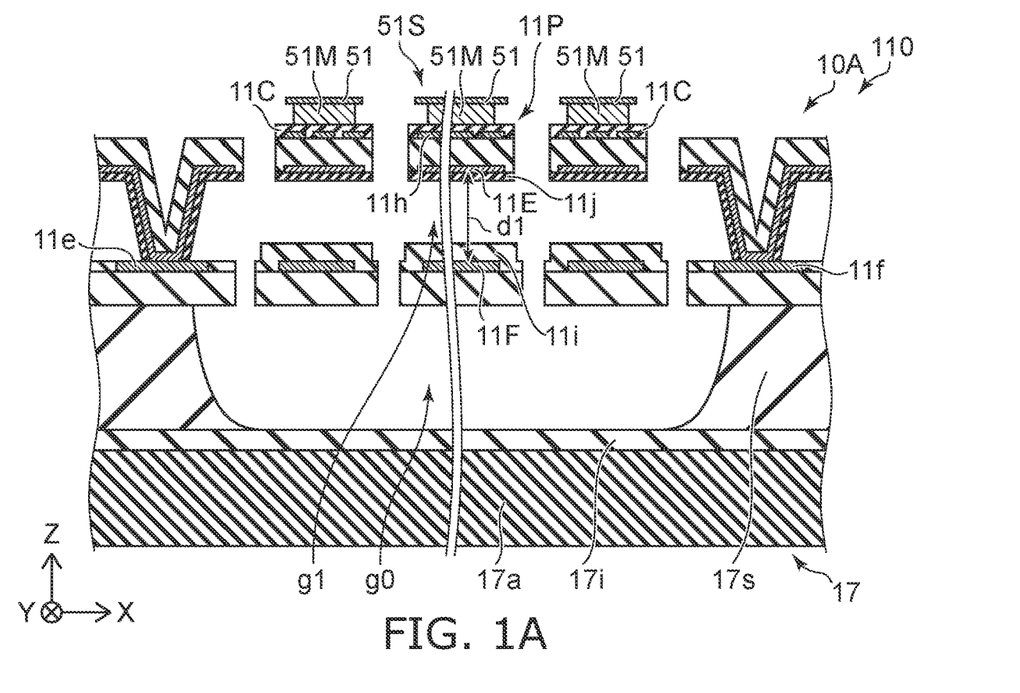
FIGS. 1A and 1B are schematic views illustrating a sensor according to a first embodiment.
Figure 1B:
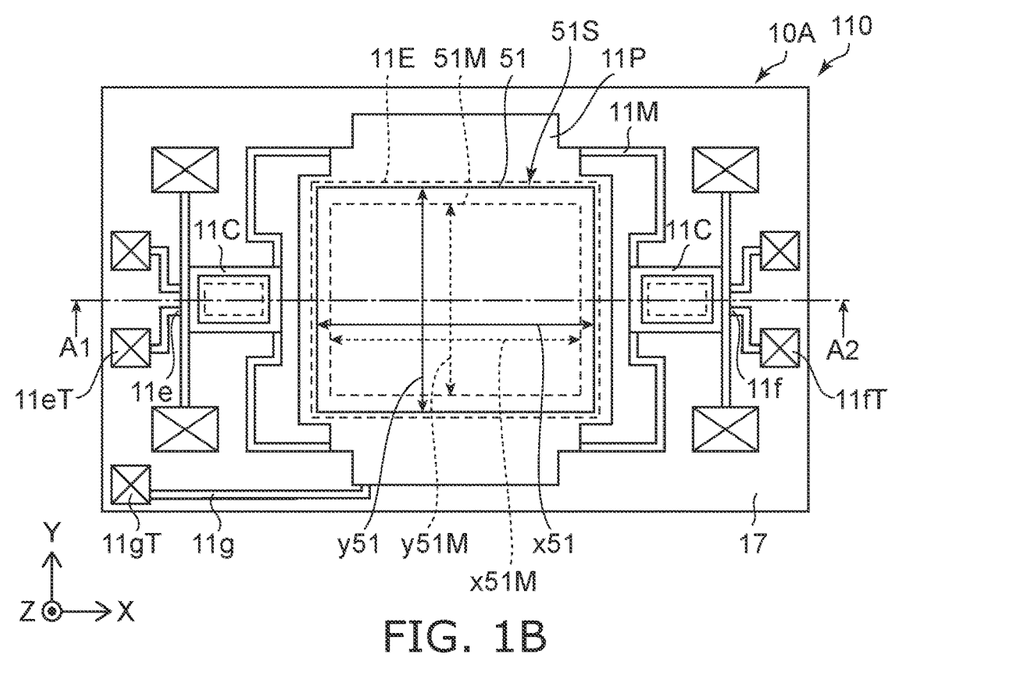

FIGS. 1A and 1B are schematic views illustrating a sensor according to a first embodiment.
FIG. 1A is a line A1-A2 cross-sectional view of FIG. 1B. FIG. 1B is a plan view.

As shown in FIG. 1A, the sensor 110 according to the embodiment includes a first sensor part 10A. The first sensor part 10A includes a first counter electrode 11F, a first movable electrode 11E, a first layer 51, and a first intermediate layer 51M. The first movable electrode 11E is between the first counter electrode 11F and the first layer 51 in a first direction.

The first direction is taken as a Z-axis direction. One direction perpendicular to the Z-axis direction is taken as an X-axis direction. A direction perpendicular to the Z-axis direction and the X-axis direction is taken as a Y-axis direction.

The first intermediate layer 51M is between the first movable electrode 11E and at least a portion of the first layer 51 in the first direction (the Z-axis direction).

A first gap g1 is located between the first counter electrode 11F and the first movable electrode 11E. As shown in FIG. 1A, an insulating part 11i may be located around the first counter electrode 11F. An insulating part 11j may be located around the first movable electrode 11E. A portion of the insulating part 11j is located between the first movable electrode 11E and the first intermediate layer 51M.

A distance d1 between the first counter electrode 11F and the first movable electrode 11E changes according to the concentration of a gas around the first sensor part 10A. The distance d1 may be taken as the distance between the insulating part 11i and the insulating part 11j for convenience. The sensor 110 is, for example, a capacitance change sensor.

For example, a structure body 51S that includes the first intermediate layer 51M and the first layer 51 can adsorb or incorporate the detection object around the first sensor part 10A. The detection object may include, for example, at least one selected from the group consisting of an element, a molecule, and an ion. The volume of the structure body 51S changes when the structure body 51S adsorbs or incorporates the detection object. The first movable electrode 11E deforms based on the change of the volume. The distance d1 between the first counter electrode 11F and the first movable electrode 11E is changed thereby. The electrical capacitance between the first counter electrode 11F and the first movable electrode 11E changes according to the change of the distance dl. The detection object can be detected by detecting electrical characteristics that correspond to the change of the electrical capacitance.

As shown in FIGS. 1A and 1B, a movable part 11P that includes the first movable electrode 11E may be connected to a connection supporter 11C via a connection part 11M. A portion of the connection supporter 11C is connected to the connection part 11M. Another portion of the connection supporter 11C is connected to a base body 17.

As shown in FIG. 1A, the structure body 51S that includes the first intermediate layer 51M and the first layer 51 described above may be provided in the connection supporter 11C. The shape of the connection supporter 11C may change due to the change of the volume of the structure body 51S according to the detection object. Thereby, the distance di may change, and the electrical capacitance between the first counter electrode 11F and the first movable electrode 11E may change. The sensor 110 is, for example, a gas sensor.

According to the embodiment, the first layer 51 includes a crystal. The first intermediate layer 51M is amorphous. Or, the crystallinity of the first intermediate layer 51M is less than the crystallinity of the first layer 51.

For example, compared to the first layer 51, the first intermediate layer 51M is easily affected by unintended elements other than the detection object. For example, the first intermediate layer 51M is easily changed by unintended elements other than the detection object. By providing the first layer 51, for example, the change of the first intermediate layer 51M caused by an unintended element can be suppressed. More stable characteristics can be maintained thereby. For example, the first layer 51 may function as a protective layer.

As shown in FIG. 1B, the width of the first layer 51 along a second direction that crosses the first direction (the Z-axis direction) is taken as a width x51. The second direction is, for example, the X-axis direction. The width of the first intermediate layer 51M along the second direction is taken as a width x51M. According to the embodiment, the width x51 is greater than the width x51M. For example, the surface area of the first layer 51 is greater than the surface area of the first intermediate layer 51M.

According to the embodiment, the first layer 51 can more effectively protect the first intermediate layer 51M. The unintentional change of the internal structure of the first intermediate layer 51M can be more effectively suppressed. A stable detection is possible. According to the embodiment, a sensor can be provided in which stable detection is possible.

The volume of the first intermediate layer 51M easily changes due to the detection object. On the other hand, the volume of the first layer 51 does not easily change. By providing the first layer 51 that has a large surface area on the first intermediate layer 51M, the deformation of the movable part 11P when the volume of the first intermediate layer 51M changes can be larger for the same surface area. Higher sensitivity is easily obtained.

As shown in FIG. 1B, the second direction that crosses the first direction (the Z-axis direction) may be the Y-axis direction. The width of the first layer 51 along the Y-axis direction is taken as a width y51. The width of the first intermediate layer 51M along the Y-axis direction is taken as a width y51M. According to the embodiment, the width y51 is greater than the width y51M. In such a case as well, for example, the surface area of the first layer 51 is greater than the surface area of the first intermediate layer 51M.

According to the embodiment, the first intermediate layer 51M includes, for example, a first element that includes at least one selected from the group consisting of Pd, Pt, and Au, and a second element that includes at least one selected from the group consisting of Si, P, and B. When the detection object is hydrogen, a stable and large volume change is easily obtained.

For example, the first intermediate layer 51M may further include a third element that includes at least one selected from the group consisting of Cu, Ag, Ni, Au, Fe, and Cr. An amorphous structure or low crystallinity is more stably and easily obtained.

The first layer 51 includes a fourth element that includes at least one selected from the group consisting of Pd, Pt, and Au.

In one example, the first intermediate layer 51M includes an alloy that includes Pd, Cu, and Si. The first layer 51 includes, for example, Pd. For example, hydrogen molecules are efficiently changed into hydrogen atoms by the catalyst effect of Pd. Thereby, the change of the volume of the first intermediate layer 51M caused by hydrogen more effectively occurs.

As shown in FIG. 1B, the first counter electrode 11F may be electrically connected with a terminal part 11gT that is located in the base body 17 by a conductive layer 11g, etc. The first movable electrode 11E may be electrically connected to a terminal part 11eT and a terminal part 11fT that are located in the base body 17 by a conductive layer 11e, a conductive layer 11f, etc.

As shown in FIG. 1A, the base body 17 may include a substrate 17a, an insulating layer 17i, and an insulating support layer 17s. The substrate 17a may be, for example, a silicon substrate, etc. The insulating layer 17i includes, for example, silicon oxide, etc. The insulating support layer 17s includes, for example, silicon nitride, etc.

As shown in FIG. 1A, a gap g0 may be located between at least a portion of the base body 17 (e.g., the insulating layer 17i) and the first counter electrode 11F (and the insulating part 11i). Low power-consumption heating is possible because the heat capacity of a heater is reduced.

As shown in FIG. 1A, the first sensor part 10A may include a first conductive layer 11h. The first conductive layer 11h is located between the first movable electrode 11E and the first intermediate layer 51M. A portion of the insulating part 11i is located between the first movable electrode 11E and the first conductive layer 11h. Another portion of the insulating part 11i is located between the first conductive layer 11h and the first intermediate layer 51M. The first conductive layer 11h is, for example, a heater. The temperature of the first conductive layer 11h is increased by a current supplied to the first conductive layer 11h. Thereby, for example, the detection object that was introduced to the first intermediate layer 51M is released from the first intermediate layer 51M. Stable detection characteristics are easily obtained.

For example, the warp of the movable part 11P may be regulated by the first conductive layer 11h. For example, the first conductive layer 11h that is located in the connection supporter 11C may be used as a heater, and the warp of the movable part 11P may be regulated by the first conductive layer 11h that is located in the movable part 11P.

Figure 2:
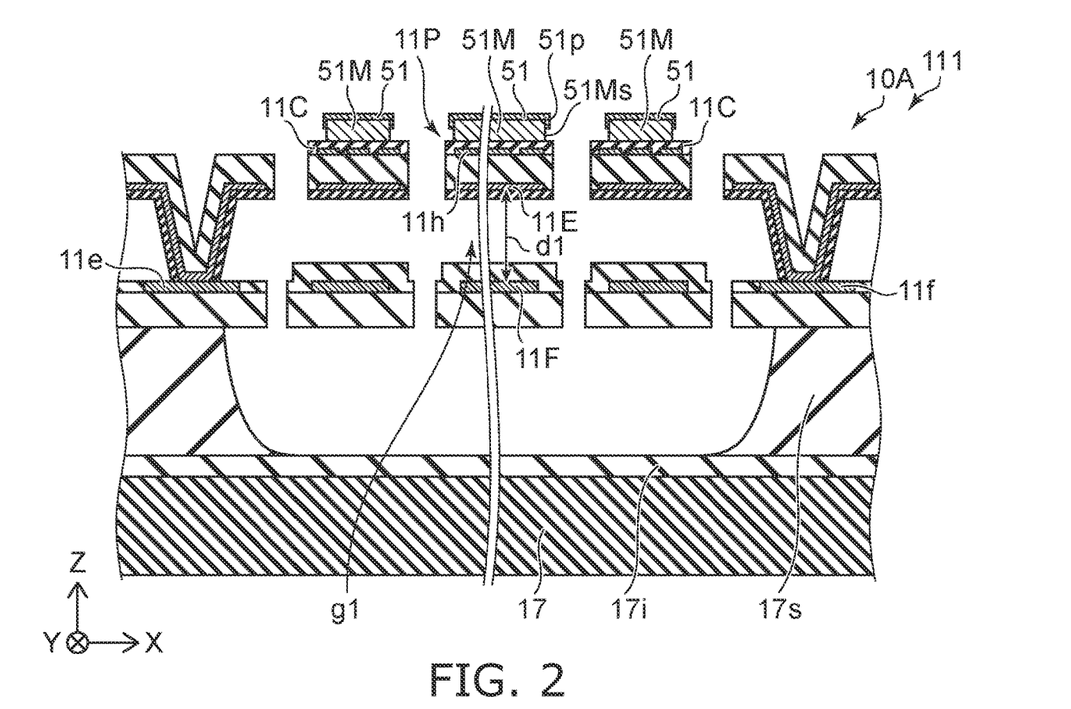
FIG. 2 is a schematic cross-sectional view illustrating a sensor according to the first embodiment.

FIG. 2 is a schematic cross-sectional view illustrating a sensor according to the first embodiment.

As shown in FIG. 2, the shape of the first layer 51 of the sensor 111 according to the embodiment is different from that of the sensor 110. Otherwise, the configuration of the sensor 111 may be similar to the sensor 110.

As shown in FIG. 2, the first intermediate layer 51M includes a first intermediate layer side surface 51Ms. The first intermediate layer side surface 51Ms crosses a plane (the X-Y plane) that crosses the first direction (the Z-axis direction). A portion of the first layer 51 overlaps the first intermediate layer side surface 51Ms in the second direction (e.g., the X-axis direction). For example, a portion of the first layer 51 covers the upper portion of the first intermediate layer side surface 51Ms in the second direction (e.g., the X-axis direction). A portion of the first intermediate layer side surface 51Ms is not covered with the first layer 51.

The characteristics of the first intermediate layer 51M become more stable due to such a first layer 51. For example, much of the detection object can be incorporated thereby. For example, the volume change of the first intermediate layer 51M increases.

For example, the upper portion of the first intermediate layer 51M is between two portions of the first layer 51. The deformation of the movable part 10P when the volume of the first intermediate layer 51M changes can be larger. Higher sensitivity is easily obtained.

Second Embodiment

Figure 3A:
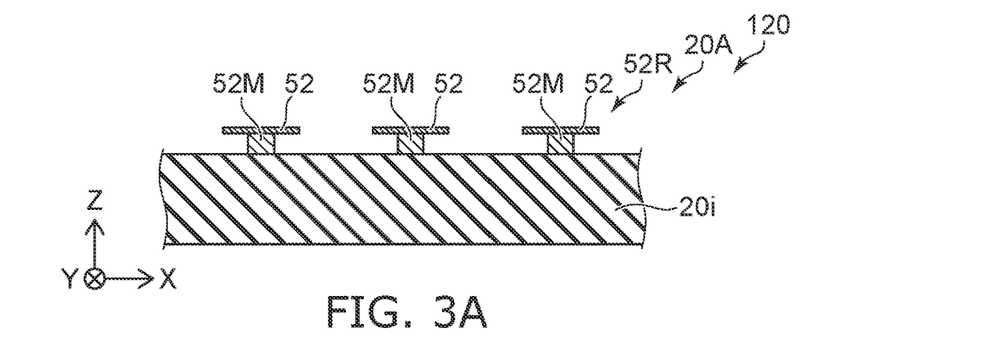
FIGS. 3A and 3B are schematic views illustrating a sensor according to a second embodiment.
Figure 3B:
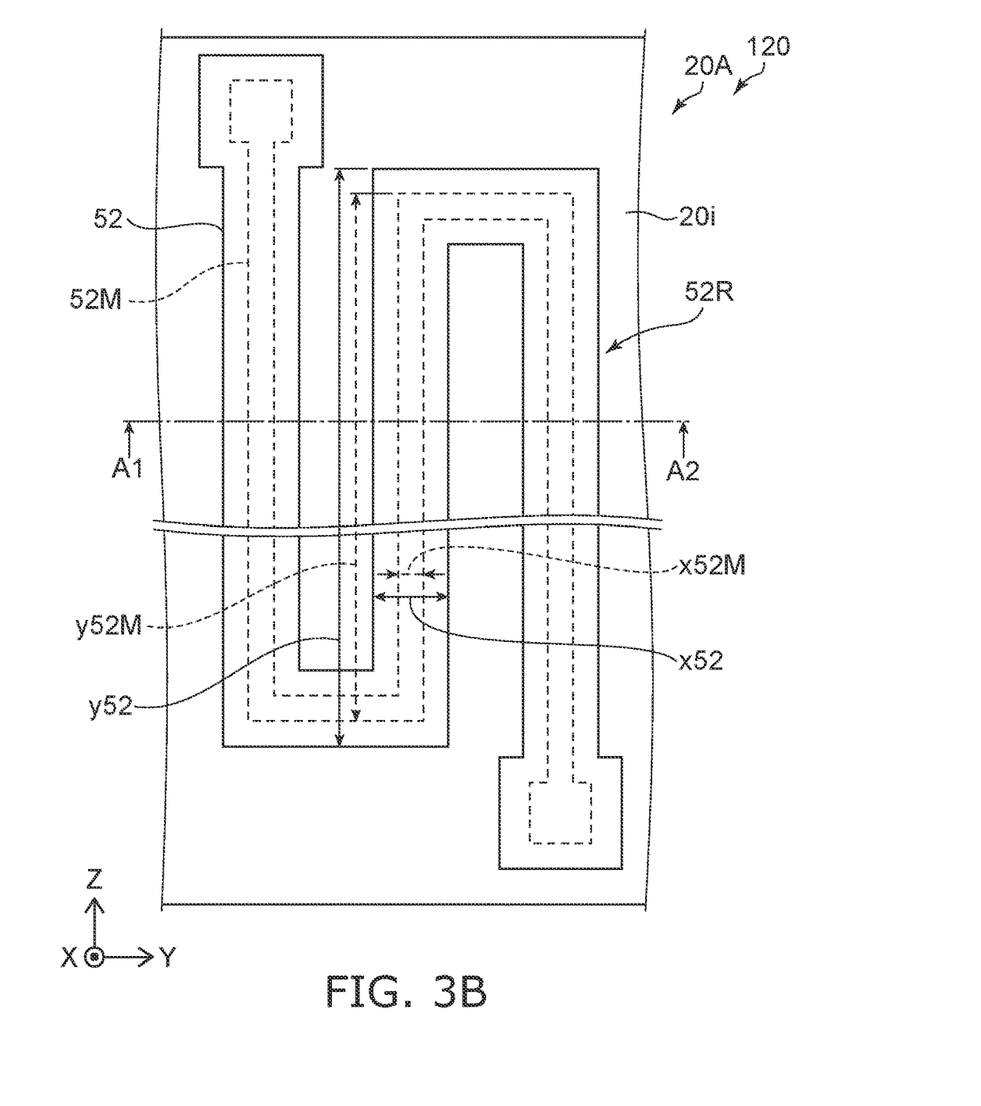

FIGS. 3A and 3B are schematic views illustrating a sensor according to a second embodiment.

FIG. 3A is a line A1-A2 cross-sectional view of FIG. 3B. FIG. 3B is a plan view.

As shown in FIG. 3A, the sensor 120 according to the embodiment includes a second sensor part 20A. The second sensor part 20A includes an insulating member 20i and a resistance member 52R. The resistance member 52R includes a second layer 52 and a second intermediate layer 52M. The second intermediate layer 52M is located between the insulating member 20i and at least a portion of the second layer 52 in the first direction (e.g., the Z-axis direction). The electrical resistance of the resistance member 52R changes according to the concentration of the gas around the second sensor part 20A.

For example, the resistance of the resistance member 52R changes when the detection object adheres to the surface of the resistance member 52R, etc. For example, the chemical properties of the surface of the resistance member 52R are changed by the detection object adhering to the surface of the resistance member 52R. For example, the characteristics of the movement of carriers (e.g., electrons) at the surface of the resistance member 52R and the vicinity of the surface change. The electrical resistance of the resistance member 52R is changed thereby. The sensor 120 is, for example, a resistance change sensor.

For example, the second layer 52 includes a crystal. The second intermediate layer 52M is amorphous. Or, the crystallinity of the second intermediate layer 52M is less than the crystallinity of the second layer 52.

As shown in FIG. 3A, the width of the second layer 52 along the second direction that crosses the first direction (the Z-axis direction) is taken as a width x52. The second direction is, for example, the X-axis direction. The width of the second intermediate layer 52M along the second direction is taken as a width x52M. The width x52 is greater than the width x52M.

The second layer 52 can more effectively protect the second intermediate layer 52M. An unintentional change of the internal structure of the second intermediate layer 52M can be more effectively suppressed.

As shown in FIG. 3B, the resistance member 52R may have a meandering structure. The width of the resistance member 52R is narrow. Thereby, the change of the electrical resistance of the resistance member 52R is set in a practically and easily useable range. The cross-sectional area of the resistance member 52R can be more stably reduced by causing the width of the second intermediate layer 52M to be less than the width of the second layer 52 when patterning the width of the resistance member 52R to be narrow.

As shown in FIG. 3B, the second direction that crosses the first direction (the Z-axis direction) may be the Y-axis direction. The width of the second layer 52 along the Y-axis direction is taken as a width y52. The width of the second Intermediate layer 52M along the Y-axis direction is taken as a width y52M. According to the embodiment, the width y52 is greater than the width y52M.

The second intermediate layer 52M includes, for example, the first element that includes at least one selected from the group consisting of Pd, Pt, and Au, and the second element that includes at least one selected from the group consisting of Si, P, and B. The second intermediate layer 52M may further include the third element that includes at least one selected from the group consisting of Cu, Ag, Ni, Au, Fe, and Cr. The second layer 52 includes, for example, the fourth element that includes at least one selected from the group consisting of Pd, Pt, and Au.

For example, the volume resistivity of the second layer 52 may be less than the volume resistivity of the second intermediate layer 52M.

For example, the thickness (the length along the Z-axis direction) of the second layer 52 may be, for example, not less than about 0.1 nm and not more than about 200 nm. For example, the thickness (the length along the Z-axis direction) of the second layer 52 is, for example, not less than the thickness of one atomic row. The thickness (the length along the Z-axis direction) of the second layer 52 may be, for example, not less than about 2 nm and not more than about 200 nm. The thickness (the length along the Z-axis direction) of the second intermediate layer 52M may be, for example, not less than 50 nm and not more than about 2 μm. The width x52 of the second layer 52 may be, for example, not less than about 10 nm and not more than about 100 nm. The length (for a meandering structure, the length along the current path) of the resistance member 52R is, for example, not less than about 1 μm and not more than about 1000 μm. The second intermediate layer 52M may have a discontinuous island configuration.

Figure 4:
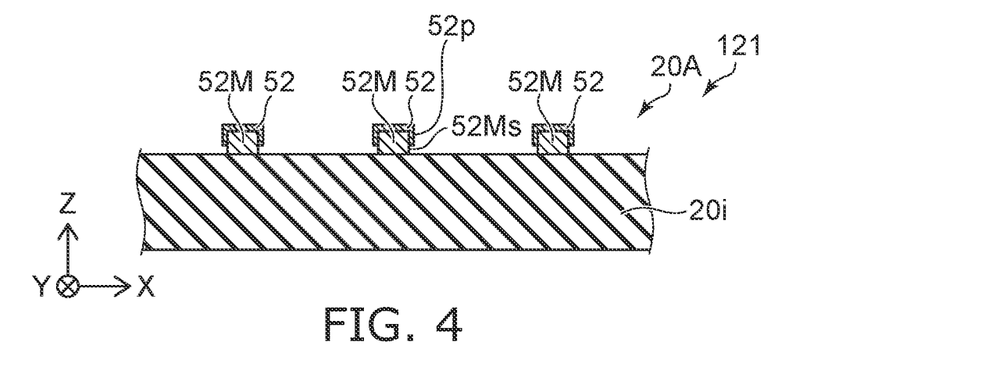
FIG. 4 is a schematic cross-sectional view illustrating a sensor according to the second embodiment.

FIG. 4 is a schematic cross-sectional view illustrating a sensor according to the second embodiment.

As shown in FIG. 4, the shape of the second layer 52 of the sensor 121 according to the embodiment is different from that of the sensor 120. Otherwise, the configuration of the sensor 121 may be similar to the sensor 120.

As shown in FIG. 4, the second intermediate layer 52M includes a second intermediate layer side surface 52Ms. The second intermediate layer side surface 52Ms crosses a plane (the X-Y plane) that crosses the first direction (the Z-axis direction). A portion of the second layer 52 overlaps the second intermediate layer side surface 52Ms in the second direction (e.g., the X-axis direction). For example, a portion of the second layer 52 covers the upper portion of the second intermediate layer side surface 52Ms in the second direction (e.g., the X-axis direction). A portion of the second Intermediate layer side surface 52Ms is not covered with the second layer 52. The characteristics of the second intermediate layer 52M become more stable due to such a second layer 52.

Figure 5:
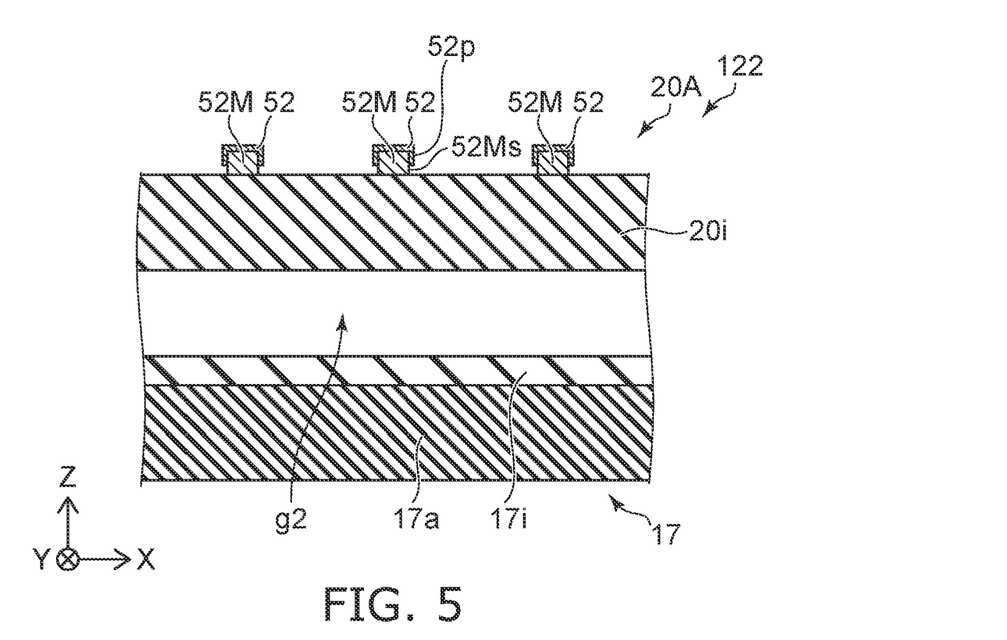
FIG. 5 is a schematic cross-sectional view illustrating a sensor according to the second embodiment.

FIG. 5 is a schematic cross-sectional view illustrating a sensor according to the second embodiment.

As shown in FIG. 5, the sensor 122 according to the embodiment includes the base body 17. Otherwise, the configuration of the sensor 122 may be similar to that of the sensor 120 or the sensor 121.

As shown in FIG. 5, the second sensor part 20A further includes the base body 17. The direction from the base body 17 toward the insulating member 20i is along the first direction (the Z-axis direction). For example, a second gap g2 may be located between the base body 17 and the insulating member 20i. For example, the effects of heat, etc., can be suppressed. More stable detection is possible.

The base body 17 may include the substrate 17a and the insulating layer 17i. The substrate 17a may be, for example, a silicon substrate, etc. The insulating layer 17i includes, for example, silicon oxide, etc.

Figure 6:
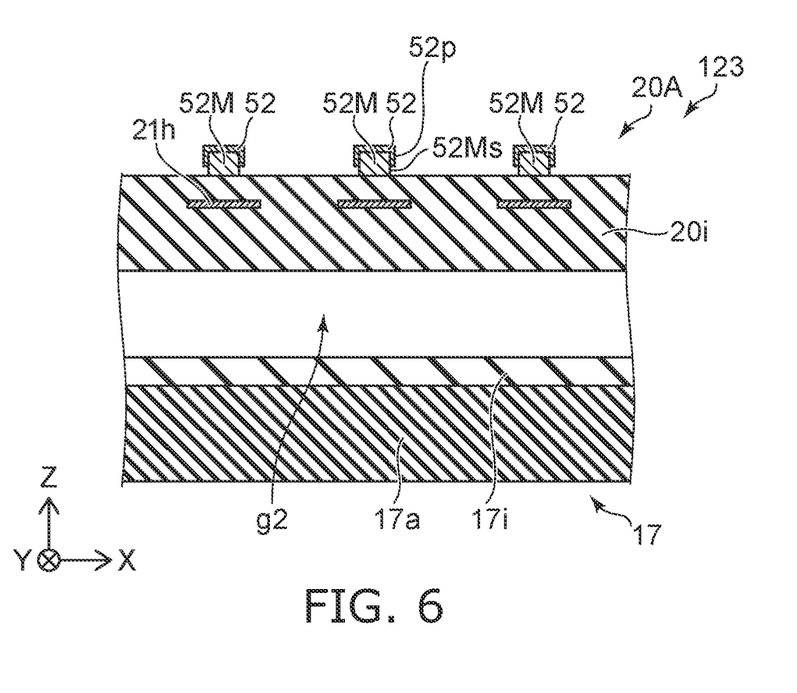
FIG. 6 is a schematic cross-sectional view illustrating a sensor according to the second embodiment.

FIG. 6 is a schematic cross-sectional view illustrating a sensor according to the second embodiment.

As shown in FIG. 6, the sensor 123 according to the embodiment includes a second conductive layer 21h. Otherwise, the configuration of the sensor 123 may be similar to those of the sensors 120 to 122.

As shown in FIG. 6, the second sensor part 20A includes the second conductive layer 21h. The second conductive layer 21h is located in the insulating member 20i. A portion of the insulating member 20i is located between the second conductive layer 21h and the second intermediate layer 52M. The second conductive layer 21h is, for example, a heater. The temperature of the second conductive layer 21h is increased by a current that is supplied to the second conductive layer 21h. Thereby, for example, the detection object that was adhered to the resistance member 52R is separated from the resistance member 52R. More stable detection characteristics are easily obtained. When the second conductive layer 21h and the second gap g2 are provided, the scattering of the heat due to the second conductive layer 21h can be suppressed. Efficient heating is easier. For example, the power consumption can be reduced.

Third Embodiment

Figure 7:
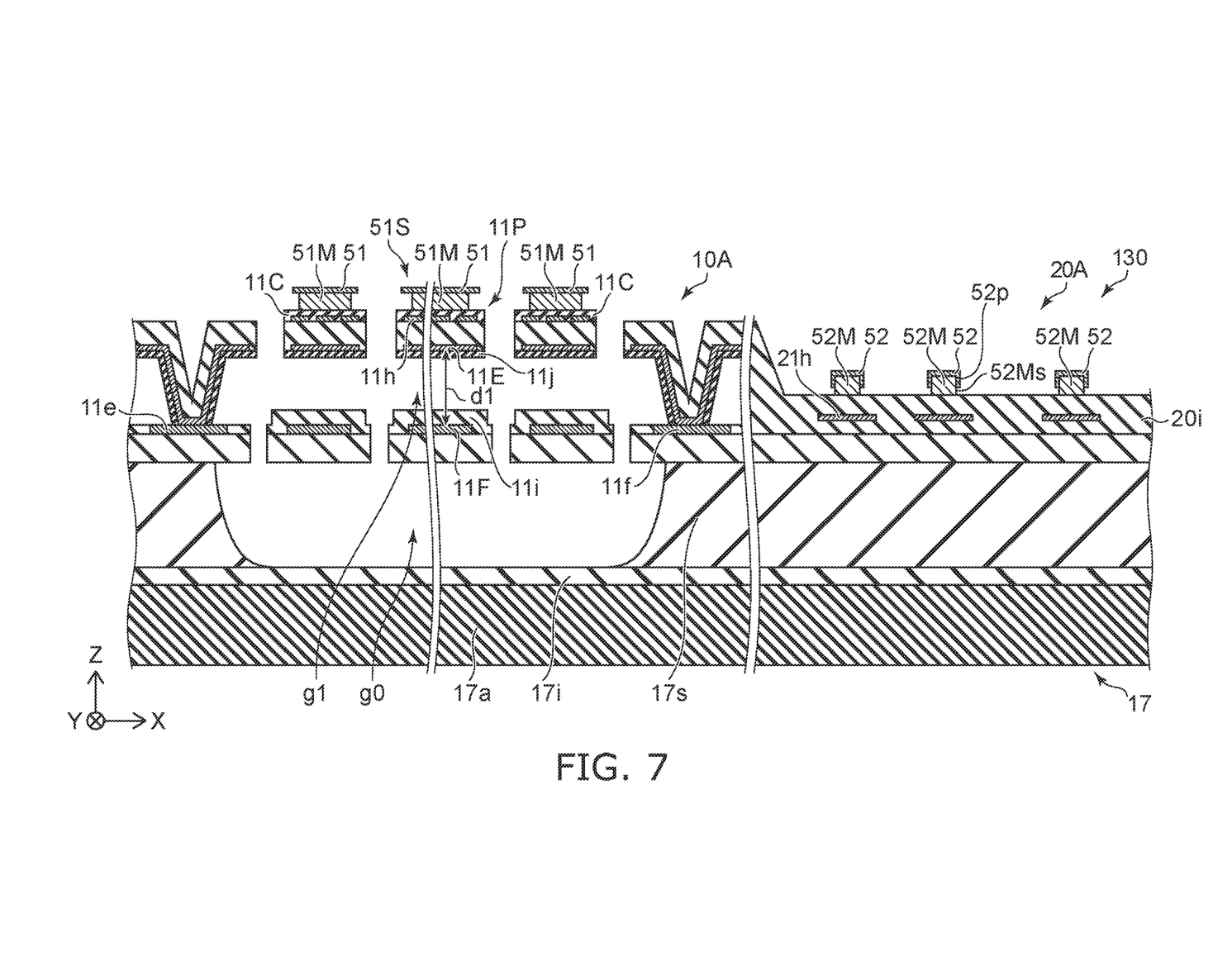
FIG. 7 is a schematic cross-sectional view illustrating a sensor according to a third embodiment.

FIG. 7 is a schematic cross-sectional view illustrating a sensor according to a third embodiment.

As shown in FIG. 7, the sensor 130 according to the embodiment includes the second sensor part 20A in addition to the first sensor part 10A. The first sensor part 10A may have the configuration described in reference to the first embodiment. The second sensor part 20A may have the configuration described in reference to the second embodiment.

The sensor 130 may include the base body 17. The direction from a portion of the base body 17 toward the first sensor part 10A is along the first direction (the Z-axis direction). The direction from another portion of the base body 17 toward the second sensor part 20A is along the first direction. For example, the first sensor part 10A and the second sensor part 20A are located on one base body 17.

For example, the second sensor part 20A has high detection sensitivity when the concentration of the detection object is low. For example, the first sensor part 10A has high detection sensitivity when the concentration of the detection object is high. By providing these multiple sensor parts, for example, the detection object can be detected in a wide concentration range.

For example, the second intermediate layer 52M includes the same material as the material included in the first intermediate layer 51M. The second layer 52 includes the same material as the material included in the first layer 51. The first intermediate layer 51M and the second intermediate layer 52M are formed of the same film. The first layer 51 and the second layer 52 are formed of the same film. The sensor 130 can be manufactured by a simple process.

For example, the first layer 51 and the first intermediate layer 51M may have the configuration illustrated in FIG. 1B. For example, the second layer 52 and the second intermediate layer 52M may have the configuration illustrated in FIG. 3B.

For example, the width x51 of the first layer 51 is greater than the width x52 of the second layer 52. The width x51M of the first intermediate layer 51M is greater than the width x52M of the second intermediate layer 52M. The first layer 51 and the first intermediate layer 51M that have wide surface areas are included in the first sensor part 10A. The second layer 52 and the second intermediate layer 52M that have fine widths are included in the second sensor part 20A. A large change of the electrical resistance is easily obtained. An electrical resistance in a practical range is easily obtained.

A first ratio of a first difference between the width x51 of the first layer 51 and the width x51M of the first intermediate layer 51M to the width x51 of the first layer 51 is (x51−x51M)/x51. A second ratio of a second difference between the width x52 of the second layer 52 and the width x52M of the second intermediate layer 52M to the width x52 of the second layer 52 is (x52−x52M)/x52. The first ratio is less than the second ratio. For example, the first difference (x51−x51M) may be substantially equal to the second difference (x52−x52M).

Such a ratio relationship is obtained when the first sensor part 10A and the second sensor part 20A are formed by the same processes.

Figure 8:
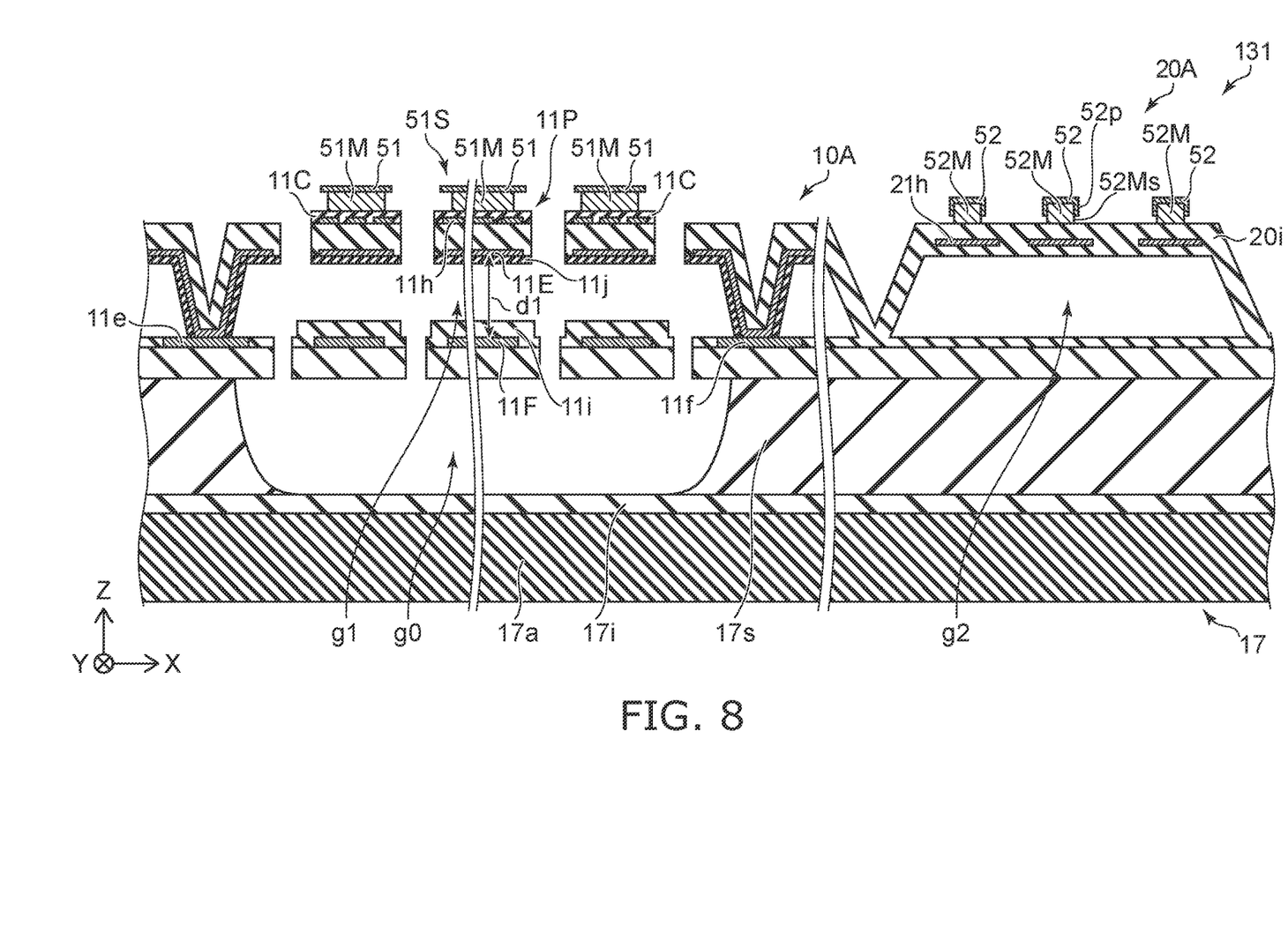
FIG. 8 is a schematic cross-sectional view illustrating a sensor according to the third embodiment.

FIG. 8 is a schematic cross-sectional view illustrating a sensor according to the third embodiment.

In the sensor 131 according to the embodiment as shown in FIG. 8, for example, the second gap g2 may be located between the base body 17 and the insulating member 20i in the second sensor part 20A. For example, the effects of heat, etc., can be suppressed. More stable detection is possible.

Figure 9:
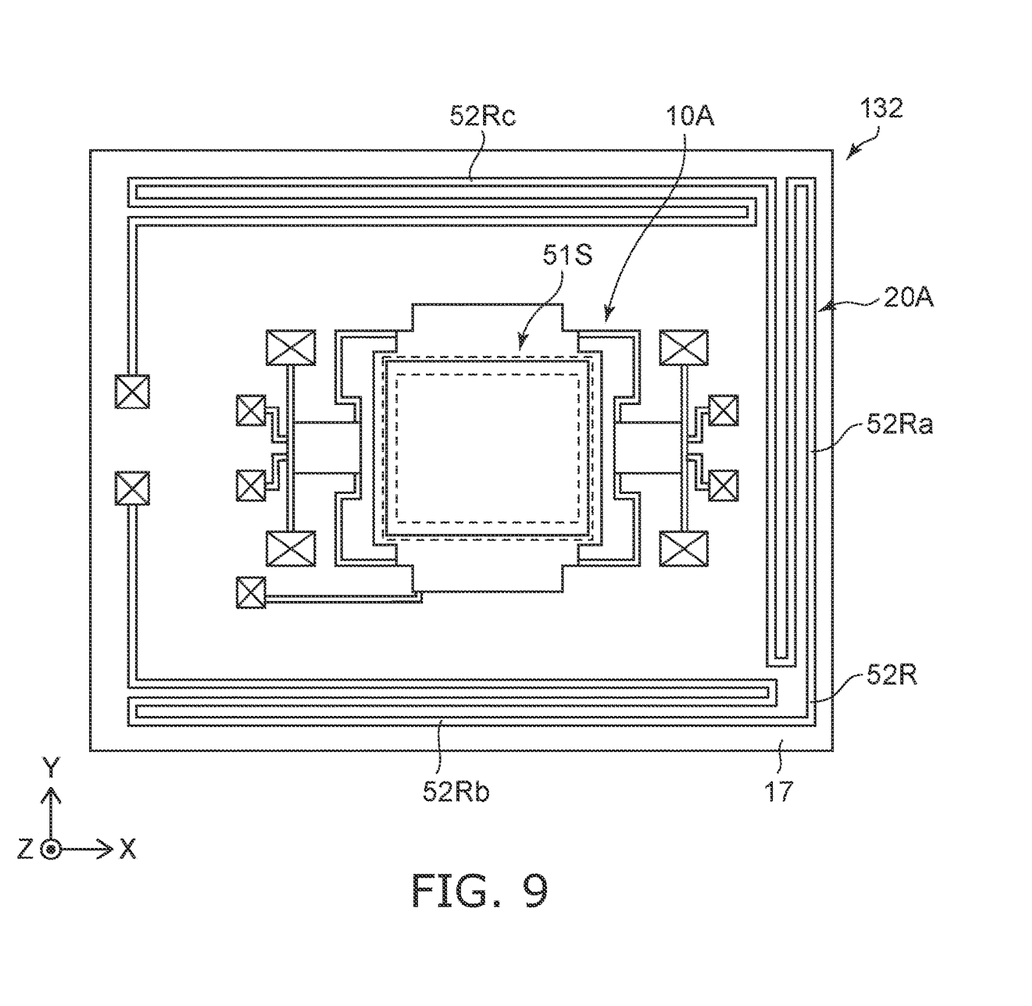
FIG. 9 is a schematic cross-sectional view illustrating a sensor according to the third embodiment.

FIG. 9 is a schematic cross-sectional view illustrating a sensor according to the third embodiment.

In the sensor 132 according to the embodiment as shown in FIG. 9, the resistance member 52R includes multiple regions. The multiple regions are, for example, a first resistance region 52Ra, a second resistance region 52Rb, a third resistance region 52Rc, etc. For example, these multiple regions each Include the second layer 52 and the second intermediate layer 52M. These multiple regions each may have meandering structures.

The direction from the first sensor part 10A toward the first resistance region 52Ra is along the second direction (e.g., the X-axis direction). The direction from the first sensor part 10A toward the second resistance region 52Rb Is along the third direction. The third direction crosses a plane (the Z-X plane) that includes the first and second directions. The third direction is, for example, the Y-axis direction. The direction from the first sensor part 10A toward the third resistance region 52Rc is along the third direction.

The length of the resistance member 52R can be increased by such a configuration. A practical resistance value is easily obtained thereby. For example, detection with high sensitivity is stable.

For example, the relationship of the widths of the first layer 51 and the first intermediate layer 51M and the relationships of the widths of the second layer 52 and the second intermediate layer 52M described above can be formed by over-etching technology. For example, a lower film that is used to form the first intermediate layer 51M and the second intermediate layer 52M is formed; and an upper film that is used to form the first layer 51 and the second layer 52 is formed on the lower film. A portion of the lower film is removed after removing a portion of the upper film. The conditions that are applied at this time are such that over-etching of the lower film occurs. The width difference is obtained thereby. For example, wet etching is applicable to the etching.

According to the embodiment, hydrogen can be detected by the first and second sensor parts 10A and 20A in a wide concentration range of, for example, 1 ppm to 2%.

Embodiments may include the following configurations (e.g., technological proposals).

Configuration 1

A sensor, comprising:
a first sensor part,
the first sensor part including a first counter electrode, a first movable electrode, a first layer, and a first intermediate layer,
the first movable electrode being between the first counter electrode and the first layer in a first direction,
the first intermediate layer being between the first movable electrode and at least a portion of the first layer in the first direction,
a first gap being located between the first counter electrode and the first movable electrode,
a distance between the first counter electrode and the first movable electrode changing according to a concentration of a gas around the first sensor part,
the first layer including a crystal,
the first intermediate layer being amorphous, or a crystallinity of the first intermediate layer being less than a crystallinity of the first layer,
a width of the first layer along a second direction being greater than a width of the first intermediate layer along the second direction,
the second direction crossing the first direction.

Configuration 2

The sensor according to Configuration 1, wherein
the first intermediate layer includes:
a first element including at least one selected from the group consisting of Pd, Pt, and Au; and
a second element including at least one selected from the group consisting of Si, P, and B.

Configuration 3

The sensor according to Configuration 2, wherein
the first intermediate layer further includes a third element including at least one selected from the group consisting of Cu, Ag, Ni, Au, Fe, and Cr.

Configuration 4

The sensor according to any one of Configurations 1 to 3, wherein
the first layer includes a fourth element including at least one selected from the group consisting of Pd, Pt, and Au.

Configuration 5

The sensor according to one of Configurations 1 to 4, wherein
the first intermediate layer includes a first intermediate layer side surface,
the first intermediate layer side surface crosses a plane crossing the first direction, and
a portion of the first layer overlaps the first intermediate layer side surface in the second direction.

Configuration 6

The sensor according to Configuration 5, wherein
a portion of the first intermediate layer side surface is not covered with the first layer.

Configuration 7

The sensor according to any one of Configurations 1 to 6, further comprising:
a second sensor part,
the second sensor part including an insulating member and a resistance member,
the resistance member including
a second layer, and
a second intermediate layer located between the insulating member and at least a portion of the second layer in the first direction,
an electrical resistance of the resistance member changing according to a concentration of a gas around the second sensor part,
the second layer including a crystal,
the second intermediate layer being amorphous, or a crystallinity of the second intermediate layer being less than a crystallinity of the second layer,
a width of the second layer along the second direction being greater than a width of the second intermediate layer along the second direction.

Configuration 8

The sensor according to Configuration 7, wherein
the second intermediate layer includes a same material as a material included in the first intermediate layer, and
the second layer includes a same material as a material included in the first layer.

Configuration 9

The sensor according to Configuration 7 or 8, wherein
the width of the first layer is greater than the width of the second layer,
the width of the first intermediate layer is greater than the width of the second intermediate layer, and
a ratio of a difference between the width of the first layer and the width of the first intermediate layer to the width of the first layer is less than a ratio of a difference between the width of the second layer and the width of the second intermediate layer to the width of the second layer.

Configuration 10

The sensor according to any one of Configurations 7 to 9, further comprising:
a base body,
a direction from a portion of the base body toward the first sensor part being along the first direction,
a direction from an other portion of the base body toward the second sensor part being along the first direction.

Configuration 11

The sensor according to Configuration 10, wherein a second gap is located between the insulating member and the other portion of the base body.

Configuration 12

A sensor, comprising:
a second sensor part,
the second sensor part including an insulating member and a resistance member,
the resistance member including
a second layer, and
a second intermediate layer located between the insulating member and at least a portion of the second layer in a first direction,
an electrical resistance of the resistance member changing according to a concentration of a gas around the second sensor part, the second layer including a crystal, the second intermediate layer being amorphous, or a crystallinity of the second intermediate layer being less than a crystallinity of the second layer, a width of the second layer along a second direction being greater than a width of the second intermediate layer along the second direction, the second direction crossing the first direction.

Configuration 13

The sensor according to Configuration 12, wherein the second intermediate layer includes:

a first element Including at least one selected from the group consisting of Pd, Pt, and Au; and a second element including at least one selected from the group consisting of Si, P, and B.

Configuration 14

The sensor according to Configuration 13, wherein the second intermediate layer further includes a third element including at least one selected from the group consisting of Cu, Ag, Ni, Au, Fe, and Cr.

Configuration 15

The sensor according to any one of Configurations 12 to 14, wherein the second layer includes a fourth element including at least one selected from the group consisting of Pd, Pt, and Au.

Configuration 16

The sensor according to any one of Configurations 12 to 15, wherein the second sensor part further includes a base body, a direction from the base body toward the insulating member is along the first direction, and a second gap is located between the base body and the insulating member.

Configuration 17

The sensor according to one of Configurations 7 to 16, wherein the second intermediate layer includes a second intermediate layer side surface that crosses the plane crossing the first direction, and a portion of the second layer overlaps the second intermediate layer side surface in the second direction.

Configuration 18

The sensor according to Configuration 17, wherein a portion of the second intermediate layer side surface is not covered with the second layer.

Configuration 19

The sensor according to any one of Configurations 7 to 18, wherein the second sensor part includes a second conductive layer located in the insulating member.

Configuration 20

The sensor according to any one of Configurations 7 to 19, wherein the resistance member includes a first resistance region and a second resistance region, a direction from the first sensor part toward the first resistance region is along the second direction, a direction from the first sensor part toward the second resistance region is along a third direction, and the third direction crosses a plane including the first and second directions.

According to embodiments, a sensor can be provided in which stable detection is possible.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as sensor parts, electrodes, layers, intermediate layers, resistance members, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:

a first sensor part, the first sensor part including a first counter electrode, a first movable electrode, a first layer, and a first intermediate layer, the first movable electrode being between the first counter electrode and the first layer in a first direction, the first intermediate layer being between the first movable electrode and at least a portion of the first layer in the first direction, a first gap being located between the first counter electrode and the first movable electrode, a distance between the first counter electrode and the first movable electrode changing according to a concentration of a gas around the first sensor part, the first layer including a crystal, the first intermediate layer being amorphous, or a crystallinity of the first intermediate layer being less than a crystallinity of the first layer, a width of the first layer along a second direction being greater than a width of the first intermediate layer along the second direction, the second direction crossing the first direction.

2. The sensor according to claim 1, wherein the first intermediate layer includes:

a first element including at least one selected from the group consisting of Pd, Pt, and Au; and a second element including at least one selected from the group consisting of Si, P, and B.

3. The sensor according to claim 2, wherein the first intermediate layer further includes a third element including at least one selected from the group consisting of Cu, Ag, Ni, Au, Fe, and Cr.

4. The sensor according to claim 1, wherein
the first layer includes a fourth element including at least one selected from the group consisting of Pd, Pt, and Au.

5. The sensor according to claim 1, wherein
the first intermediate layer includes a first intermediate layer side surface,
the first intermediate layer side surface crosses a plane crossing the first direction, and
a portion of the first layer overlaps the first intermediate layer side surface in the second direction.

6. The sensor according to claim 5, wherein
a portion of the first intermediate layer side surface is not covered with the first layer.

7. The sensor according to claim 1, further comprising:
a second sensor part,
the second sensor part including an insulating member and a resistance member,
the resistance member including
  a second layer, and
  a second intermediate layer located between the insulating member and at least a portion of the second layer in the first direction,
an electrical resistance of the resistance member changing according to a concentration of a gas around the second sensor part,
the second layer including a crystal,
the second intermediate layer being amorphous, or a crystallinity of the second intermediate layer being less than a crystallinity of the second layer,
a width of the second layer along the second direction being greater than a width of the second intermediate layer along the second direction.

8. The sensor according to claim 7, wherein
the second intermediate layer includes a same material as a material included in the first intermediate layer, and
the second layer includes a same material as a material included in the first layer.

9. The sensor according to claim 7, wherein
the width of the first layer is greater than the width of the second layer,
the width of the first intermediate layer is greater than the width of the second intermediate layer, and
a ratio of a difference between the width of the first layer and the width of the first intermediate layer to the width of the first layer is less than a ratio of a difference between the width of the second layer and the width of the second Intermediate layer to the width of the second layer.

10. The sensor according to claim 7, further comprising:
a base body,
a direction from a portion of the base body toward the first sensor part being along the first direction,
a direction from an other portion of the base body toward the second sensor part being along the first direction.

11. The sensor according to claim 10, wherein a second gap is located between the insulating member and the other portion of the base body.

12. The sensor according to claim 7, wherein
the second intermediate layer includes a second intermediate layer side surface that crosses the plane crossing the first direction, and
a portion of the second layer overlaps the second intermediate layer side surface in the second direction.

13. The sensor according to claim 12, wherein
a portion of the second intermediate layer side surface is not covered with the second layer.

14. The sensor according to claim 7, wherein
the second sensor part includes a second conductive layer located in the Insulating member.

15. The sensor according to claim 7, wherein
the resistance member includes a first resistance region and a second resistance region,
a direction from the first sensor part toward the first resistance region is along the second direction,
a direction from the first sensor part toward the second resistance region is along a third direction, and
the third direction crosses a plane Including the first and second directions.

16. A sensor, comprising:
a second sensor part,
the second sensor part including an insulating member and a resistance member,
the resistance member including
  a second layer, and
  a second intermediate layer located between the insulating member and at least a portion of the second layer in a first direction,
an electrical resistance of the resistance member changing according to a concentration of a gas around the second sensor part,
the second layer including a crystal,
the second intermediate layer being amorphous, or a crystallinity of the second intermediate layer being less than a crystallinity of the second layer,
a width of the second layer along a second direction being greater than a width of the second intermediate layer along the second direction,
the second direction crossing the first direction.

17. The sensor according to claim 16, wherein
the second intermediate layer includes:
  a first element including at least one selected from the group consisting of Pd, Pt, and Au; and
  a second element including at least one selected from the group consisting of Si, P, and B.

18. The sensor according to claim 17, wherein
the second intermediate layer further includes a third element including at least one selected from the group consisting of Cu, Ag, Ni, Au, Fe, and Cr.

19. The sensor according to claim 16, wherein
the second layer includes a fourth element including at least one selected from the group consisting of Pd, Pt, and Au.

20. The sensor according to claim 16, wherein
the second sensor part further includes a base body,
a direction from the base body toward the insulating member is along the first direction, and
a second gap is located between the base body and the insulating member.

\* \* \* \* \*

UNITED STATES PATENT AND TRADEMARK OFFICE
CERTIFICATE OF CORRECTION

PATENT NO. : 11,493,471 B2
APPLICATION NO. : 17/407050
DATED : November 8, 2022
INVENTOR(S) : Yumi Hayashi It is certified that error appears in the above-identified patent and that said Letters Patent is hereby corrected as shown below:

In the Claims

Claim 9, Column 13, Line 50, "Intermediate" should be --intermediate--.

Claim 14, Column 14, Line 12, "Insulating" should be --insulating--.

Signed and Sealed this
Ninth Day of May, 2023

*Katherine Kelly Vidal*

Katherine Kelly Vidal
*Director of the United States Patent and Trademark Office*